(12) United States Patent
Someya et al.

(10) Patent No.: US 12,333,851 B2
(45) Date of Patent: Jun. 17, 2025

(54) OPTICAL SENSOR

(71) Applicant: The University of Tokyo, Tokyo (JP)

(72) Inventors: Takao Someya, Tokyo (JP); Ikue Kawashima, Tokyo (JP)

(73) Assignee: The University of Tokyo, Tokyo (JP)

( * ) Notice: Subject to any disclaimer, the term of this patent is extended or adjusted under 35 U.S.C. 154(b) by 12 days.

(21) Appl. No.: 17/788,873

(22) PCT Filed: Dec. 25, 2020

(86) PCT No.: PCT/JP2020/048849
§ 371 (c)(1),
(2) Date: Jun. 24, 2022

(87) PCT Pub. No.: WO2021/132605
PCT Pub. Date: Jul. 1, 2021

(65) Prior Publication Data
US 2023/0051655 A1    Feb. 16, 2023

(30) Foreign Application Priority Data
Dec. 27, 2019  (JP) .................................. 2019-238112

(51) Int. Cl.
*G06V 40/145*     (2022.01)
*A61B 5/1171*     (2016.01)

(52) U.S. Cl.
CPC .......... *G06V 40/145* (2022.01); *A61B 5/1171* (2016.02)

(58) Field of Classification Search
CPC ....... G06V 40/145; A61B 5/1171; G06T 1/00; G01N 21/17; G07C 9/00
See application file for complete search history.

(56) References Cited

U.S. PATENT DOCUMENTS

| 6,144,511 | A  | * | 11/2000 | Umetsu  | G06V 40/1324 |
| | | | | | 359/833 |
| 9,829,614 | B2 | * | 11/2017 | Smith  | G02B 5/208 |
| 10,579,847 | B2 | * | 3/2020 | Cho  | G06V 40/1318 |
| 11,416,074 | B1 | * | 8/2022 | Trincia  | G02B 1/045 |

(Continued)

FOREIGN PATENT DOCUMENTS

| CN | 209170491 U | 7/2019 |
| JP | 2002123822 A | 4/2002 |

(Continued)

OTHER PUBLICATIONS

International Search Report and Written Opinion for International Patent Application No. PCT/US2020/048849 dated Mar. 23, 2021, 9 pages.

*Primary Examiner* — John B Strege (74) *Attorney, Agent, or Firm* — Dorsey & Whitney LLP (57) ABSTRACT

Uniform light irradiation to the measurement object is realized, and it is possible to obtain high resolution image information, to provide a reflective optical sensor. An optical sensor comprises a light irradiation unit for performing uniform light irradiation with respect to the measurement object, the viewing angle control plate for limiting the direction of the reflected light in the measurement object to the predetermined direction, a light detecting unit for acquiring image information showing the distribution of the reflected light obtained through the viewing angle control plate. The viewing angle control plate is a louver array film or a fiber optic plate.

19 Claims, 6 Drawing Sheets

(56) References Cited

U.S. PATENT DOCUMENTS

| | | | | |
|---|---|---|---|---|
| 2003/0044051 | A1* | 3/2003 | Fujieda | G06V 40/40 382/124 |
| 2016/0218238 | A1* | 7/2016 | Eguchi | G02B 6/0078 |
| 2020/0144435 | A1* | 5/2020 | Gaides | G02B 5/223 |
| 2021/0081639 | A1* | 3/2021 | Sun | G06V 40/1318 |
| 2022/0059619 | A1* | 2/2022 | Kubota | G06F 3/01 |
| 2023/0057777 | A1* | 2/2023 | Yogeeswaran | G02B 3/08 |

FOREIGN PATENT DOCUMENTS

| | | | |
|---|---|---|---|
| JP | 2005209141 | A | 8/2005 |
| JP | 2007117397 | A | 5/2007 |
| JP | 2009163408 | A | 7/2009 |
| JP | 2018534803 | A | 11/2018 |
| JP | 2019128630 | A | 8/2019 |

\* cited by examiner

OPTICAL SENSOR

CROSS-REFERENCE TO RELATED APPLICATIONS

This application is the national stage application of International Patent Application No. PCT/JP2020/048849 filed on Dec. 25, 2020 and entitled "Optical Sensor", which claims priority to Japanese Patent Application No. 2019-238112 filed on Dec. 27, 2019 and entitled "Optical Sensor" the entire contents of which are hereby incorporated by reference herein in their entireties.

TECHNICAL FIELD

The present invention relates to an optical sensor.

BACKGROUND ART

Among biometric authentication techniques, vein authentication in which authentication is performed using a vein pattern is known as a technique capable of performing high-precision authentication. As optical sensors for performing vein authentication, there are a transmission type sensor (for example, refer to Patent Document 1) and a reflection type sensor (for example, refer to Patent Document 2).

In the transmission type sensor, the light source unit is disposed on one side of the measurement object, the light receiving unit is disposed on the other side. Light generated by the light source unit is transmitted through the measurement object and is received by the light receiving unit. At this time, a part of the light passing through the measurement object is absorbed or scattered by the vein, whereby a vein pattern is obtained.

In the reflection type sensor, the light source unit and the light receiving unit are disposed on one side of the measurement object. The light generated by the light source unit is absorbed or scattered by the vein, whereby a vein pattern is obtained in the light receiving unit.

Patent Document 1: JP2009-163408A
Patent Document 2: JP2019-128630A

Problems to be Solved by the Invention

However, in the transmission type sensor of the above-mentioned conventional example, when absorption or scattering in a part other than the vein is large in the measurement object, the light does not reach the light receiving unit. Accordingly, the measurement cannot be performed in some cases.

On the other hand, in the reflection type sensor of the above-mentioned conventional example, since the light source unit is provided around the light receiving unit, there is a case where uniform light irradiation is impossible.

This invention is made in consideration of the above-described point. An object of the present invention is to provide a reflection type optical sensor capable of realizing uniform light irradiation to a measurement object and obtaining image information with high resolution.

Solutions to the Problems

To achieve the above-described object, the optical sensor of the present invention is configured to include a light irradiation unit for performing uniform light irradiation to the measurement object, a view angle control plate for limiting the direction of the reflected light from the measurement object in a predetermined direction, and a light detection unit for acquiring image information indicating the distribution of the reflected light obtained through the viewing angle control plate.

According to a preferred embodiment of the optical sensor of the present invention, the viewing angle control plate is a louver array film or a fiber optic plate. Further, the viewing angle control plate is preferably provided between the light irradiation unit and the light detection unit, and the light irradiation unit is preferably provided between the measurement object and the viewing angle control plate.

In a preferred embodiment of the optical sensor of the present invention, the light irradiating unit includes a light source and a light guide plate, and the light emitted by the light source spreads throughout the inside of the light guide plate. Further, on one main surface of the light guide plate, a regularly modulated portion is formed over the entire surface. The condition of total reflection in the modulation part is different from that in the non-modulated part which is a part other than the modulation part.

The light guide plate is preferably composed of materials having Young's modulus of 1 [MPa] or more and 1000 [MPa] or less of the material. The thickness of the light guide plate is preferably 100 [μm] or more and 1 [mm] or less.

The viewing angle control plate is preferably composed of a material having Young's modulus of 1 [MPa] or more and 1000 [MPa] or less. The thickness of the viewing angle control plate is preferably 1 [mm] or less.

Effects of the Invention

According to the optical sensor of the present invention, the above-described configuration realizes uniform light irradiation to the measurement object and makes it possible to obtain image information with high resolution.

DETAILED DESCRIPTION OF THE INVENTION

While the following describes embodiments of the invention with reference to the drawings, shapes, sizes, and positional relationships of respective components are only schematically illustrated for understanding the invention. While the following describes preferred exemplary configurations of the invention, materials, numerical conditions, and the like of respective components are merely preferable examples. Therefore, the invention is not limited to the following embodiments, and many changes or modifications that can achieve the effects of the invention can be made without departing from the scope of the configuration of the invention.

Figure 1:
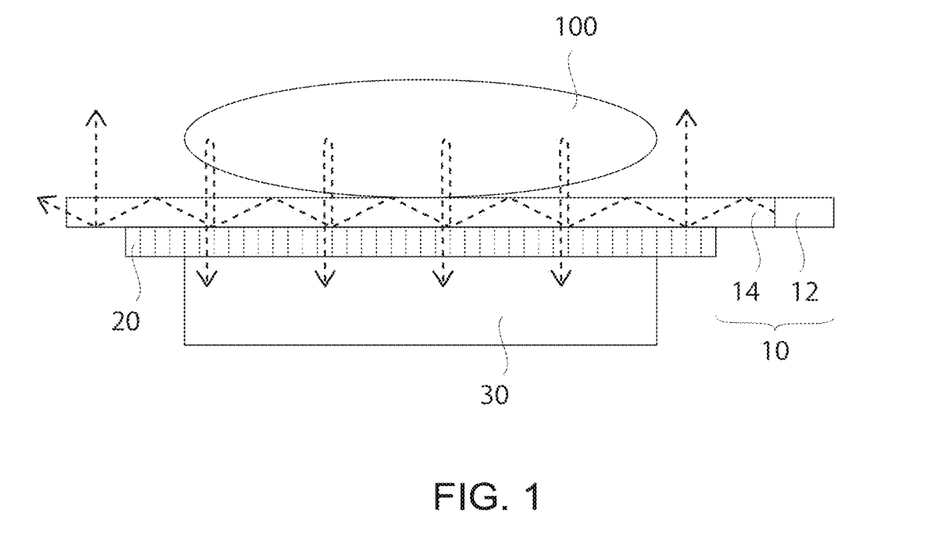
FIG. 1 is a schematic diagram for explaining an optical sensor of the present invention.

Referring to FIG. 1, an optical sensor of the present invention will be described. FIG. 1 is a schematic diagram for explaining an optical sensor of the present invention.

The light sensor of the present invention is configured to include the light irradiation unit 10, the viewing angle control plate 20 and a light detecting unit 30, and is a light sensor of the reflection type. Light irradiation unit 10, the viewing angle control plate 20, and the light detecting unit 30 are disposed on one side of the measurement object 100. In the optical sensor, the reflected light at the measurement object 100 among the light which is irradiated from the light irradiation unit 10 to the measurement object 100 is detected by the light detection unit 30.

Light irradiation unit 10 is configured to include a light source 12 and the light guide plate 14.

Light source 12 is, for example, LED (Light Emission Diode) that emit infrared. Light source 12 is attached to the side surface of the light guide plate 14. Light emitted by the LED emitting infrared light (infrared LED) is sent to the light guide plate 14.

Light sent to the light guide plate 14 is input to the inside of the light guide plate 14 from the side surface of the light guide plate 14 and propagates inside of the light guide plate 14 while totally reflecting in the two main surfaces. As a result, light input to the inside of the light guide plate 14 spreads over the entire interior of the light guide plate 14. FIG. 1 shows an example which the light source 12 is attached to the side surface of the light guide plate 14. The light input to the inside of the light guide plate 14 is sufficient to spread over the entire interior of the light guide plate 14. The light source 12 may be attached to the main surface of the light guide plate 14.

Figure 2:
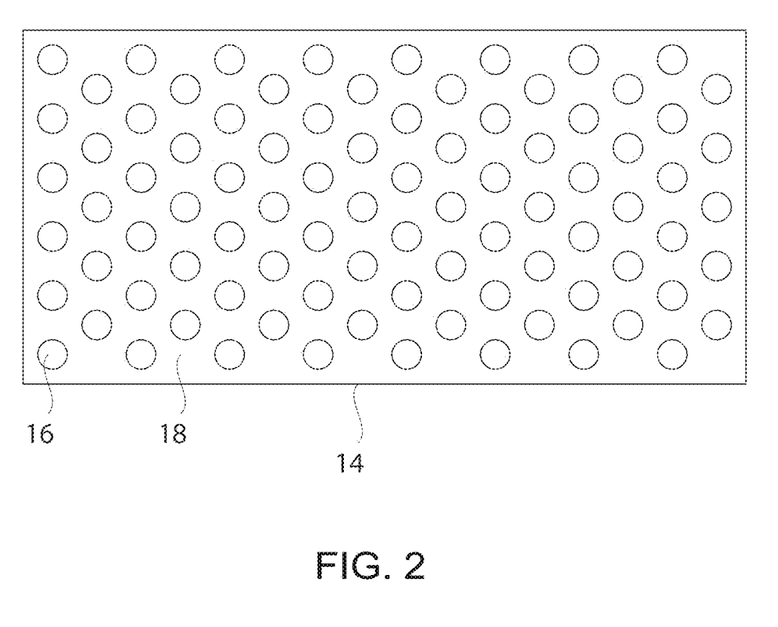
FIG. 2 is a plan view showing a configuration example of a light guide plate, showing one of the main surfaces.

On one main surface of the light guide plate 14, the modulation part 16 is regularly provided over the entire surface. FIG. 2 is a plan view showing a configuration example of the light guide plate 14 and shows one of the main surfaces.

The condition of total reflection in the modulation part 16 of the light guide plate 14 is different from that in the non-modulating part 18 which is a part other than the modulation part 16. Therefore, the light reaching the modulation part 16 is output to the outside of the light guide plate 14. Light output to the outside of the light guide plate 14 is sent to the measurement object 100 such as a living body. With a modulation pattern which the modulation part 16 is provided regularly over the entire main surface of the light guide plate 14, uniformly light is irradiated from the entire surface of one of the main surfaces of the light guide plate 14. As a result, uniform light irradiation to the measurement object 100 is realized. In order to irradiate uniformly light, a modulation unit 16 is preferably provided denser as it is farther from the light source 12.

The light guide plate 14 is made of any suitable material capable of transmitting light emitted by the light source 12, such as polyurethane, silicone, or acrylic. The modulation pattern can be formed by a conventionally known method such as forming a lens-shaped convex portion as the modulation part 16 by an inkjet technique.

Here, an example will be described in which the measurement object 100 is a human wrist and the optical sensor measures the vein pattern of the wrist. In this case, it is preferable that the light guide plate 14 has flexibility so as to be in close contact with the wrist. Therefore, the light guide plate is preferably composed of materials having Young's modulus of 1 [MPa] or more and 1000 [MPa] or less of the material, and the thickness of the light guide plate is preferably 100 [μm] or more and 1 [mm] or less.

The light irradiated to the measurement object 100 from the light guide plate 14 is reflected on the surface or inside of the measurement object 100. The reflected light is transmitted through the light guide plate 14 and is sent to the light detecting unit 30. In the case where the measurement object 100 is a wrist, the reflection intensity in the region where the vein exists inside the wrist is weaker than that in the region where the vein does not exist, because the portion inside the wrist where the vein exists absorbs infrared light. As a result, the image of the region where the vein exists becomes darker than the image of the other region and is recognized by the optical sensor as the vein image.

The light reflected by the measurement object 100 is input into the light detecting unit 30. The light detection unit 30 acquires image information indicating a vein pattern from the input light, and outputs the image information. The light detection unit 30 may have any suitable conventionally known configuration, for example, a CMOS image sensor that converts an optical signal into an electric signal is used. Here, although omitted figures and detailed description, a protective glass for protecting CMOS image sensor is provided on the input side of the light detecting unit 30.

It can be configured that the electric signal obtained by CMOS image sensor can output to the outside of the optical sensor as image information. In this case, the image information may be displayed on an external personal computer or the like.

On the input side of the light detecting unit 30, the viewing angle control plate 20 is provided. The viewing angle control plate 20 limits the direction of the reflected light from the measurement object 100 and input to the light detection unit 30 to the light in a predetermined direction. By providing the viewing angle control plate 20 on the input side of the light detecting unit 30, since the direction of the light input to the light receiving surface of the light detecting unit 30 is limited to a direction substantially perpendicular to the light receiving surface. As a result, a clearer vein pattern is obtained.

As a method for obtaining a clear image, there is a method using the principle of a pinhole camera other than the method using the viewing angle control plate used in the present invention. However, in the pinhole camera, it is necessary to provide a considerable distance between the measured object and the pinhole, and between the pinhole and the optical sensor. Therefore, in the pinhole camera, a thin optical sensor such as the optical sensor of the present invention cannot be realized. The image obtained by the pinhole camera is an inverted image, which is different from the image obtained by the present invention.

The viewing angle control plate 20 is composed of a louver array film (LAF) or a fiber optic plate (FOP). The LAF is a film known as a privacy film or a privacy sheet, which has light shielding portions in an array shape and transmits light in a predetermined direction. LAF transmits light in a range of viewing angle determined by the spacing of the light shielding portion and the thickness of the LAF as light in a predetermined direction.

Further, FOP is a plate composed by bundling optical fibers of several μm diameter. The propagation direction of the light of the optical fiber corresponds to the thickness direction of the FOP. FOP transmits light in a direction within an angle determined by the total reflection conditions of the optical fibers comprising the FOPs.

Therefore, the predetermined direction of light transmitted through the viewing angle control plate 20 is a direction substantially parallel to the normal direction of the incident surface of the viewing angle control plate 20 and the light detecting unit 30.

Similar to the light guide plate 14, the viewing angle control plate is preferably composed of a material having Young's modulus of 1 [MPa] or more and 1000 [MPa] or less. The thickness of the viewing angle control plate 20 is preferably 1 [mm] or less. The design conditions of the FOP, such as the thickness of the FOP and the diameter of the optical fibers configuring the FOP, can be determined by the required flexibility and resolution. The numerical aperture NA which is an angular range in which light incident on the FOP is propagated is preferably 0.1 or more and 0.7 or less.

The photodetector 30 may also have flexibility. As a CMOS image sensor included in the photo receiving unit 30, a sensor having flexibility using a polyimide film or the like as a board is known. Further, the electrical circuit used to operate CMOS image sensor can be made flexible. For this purpose, the arithmetic elements can be placed on the film-shaped substrate. In this manner, the light detection unit 30 can also be made flexible.

In FIG. 1, an example in which the viewing angle control plate 20 is provided between the light irradiation unit 10 and the light detection unit 30 is illustrated, but the present invention is not limited thereto.

Figure 3:
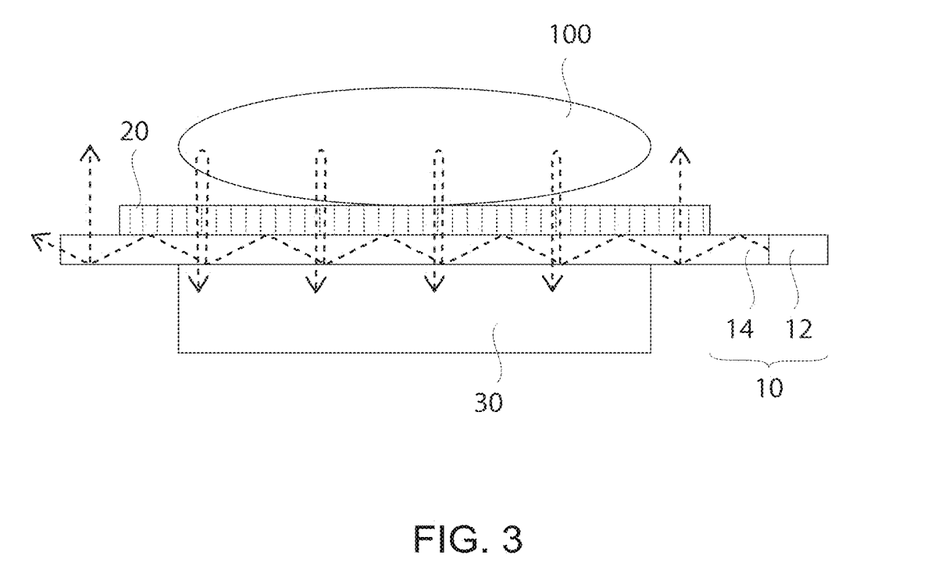
FIG. 3 is a schematic diagram showing another configuration example of an optical sensor of the present invention.

Referring to FIG. 3, another configuration example of the optical sensor will be described. FIG. 3 is a schematic diagram showing another configuration example of the optical sensor of the present invention.

In another configuration example of the optical sensor, the viewing angle control plate 20 is provided between the measurement object 100 and the light irradiation unit 10. In this case, the light output from the light irradiation unit 10 is sent to the measurement object 100 via the viewing angle control plate 20. Then, the light reflected by the measurement object 100 is sent to the light detection unit 30 via the viewing angle control plate 20 and the light irradiation unit 10 in this order.

EXAMPLES

The optical sensor can be incorporated, for example, in a wrist sphygmomanometer. In this case, the optical sensor is attached to the cuff portion of the wrist-type sphygmomanometer. With this configuration, biometric authentication based on the vein pattern can be performed when blood pressure is measured. As a result, the blood pressure measurement data and the subject of measurement are more easily and reliably associated with each other than before.

Experimental Results

Figure 4:
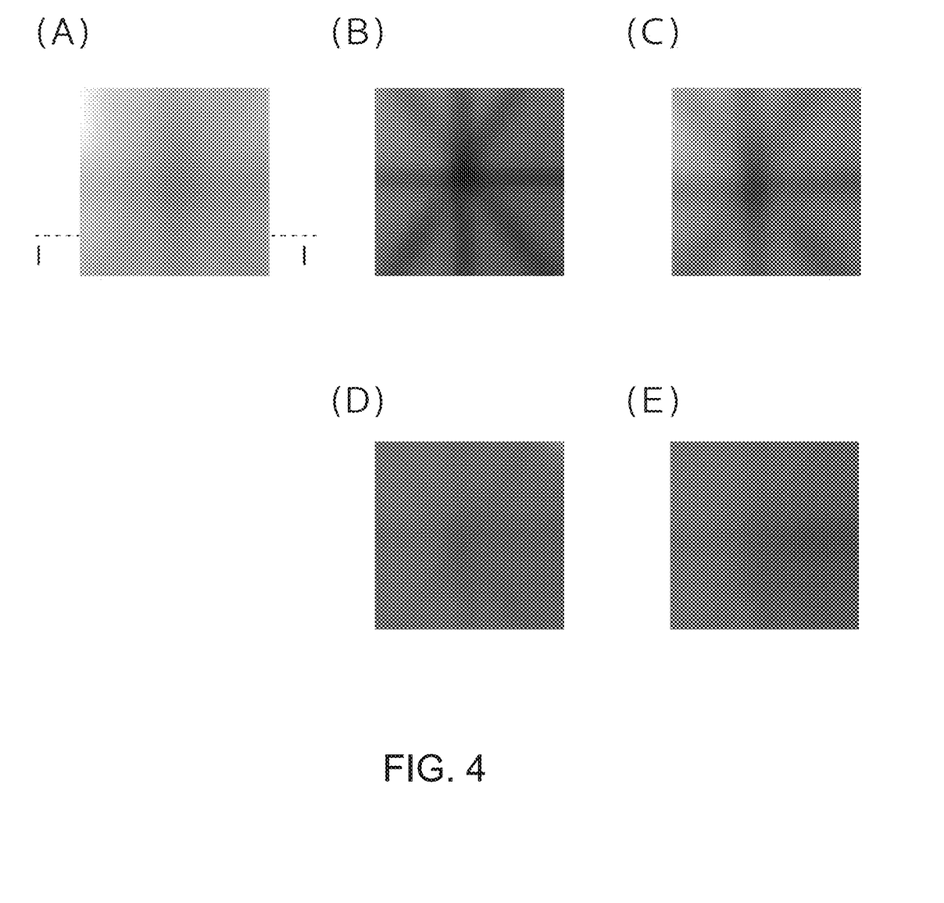
FIG. 4 is a diagram showing an image obtained in an experiment.
Figure 5:
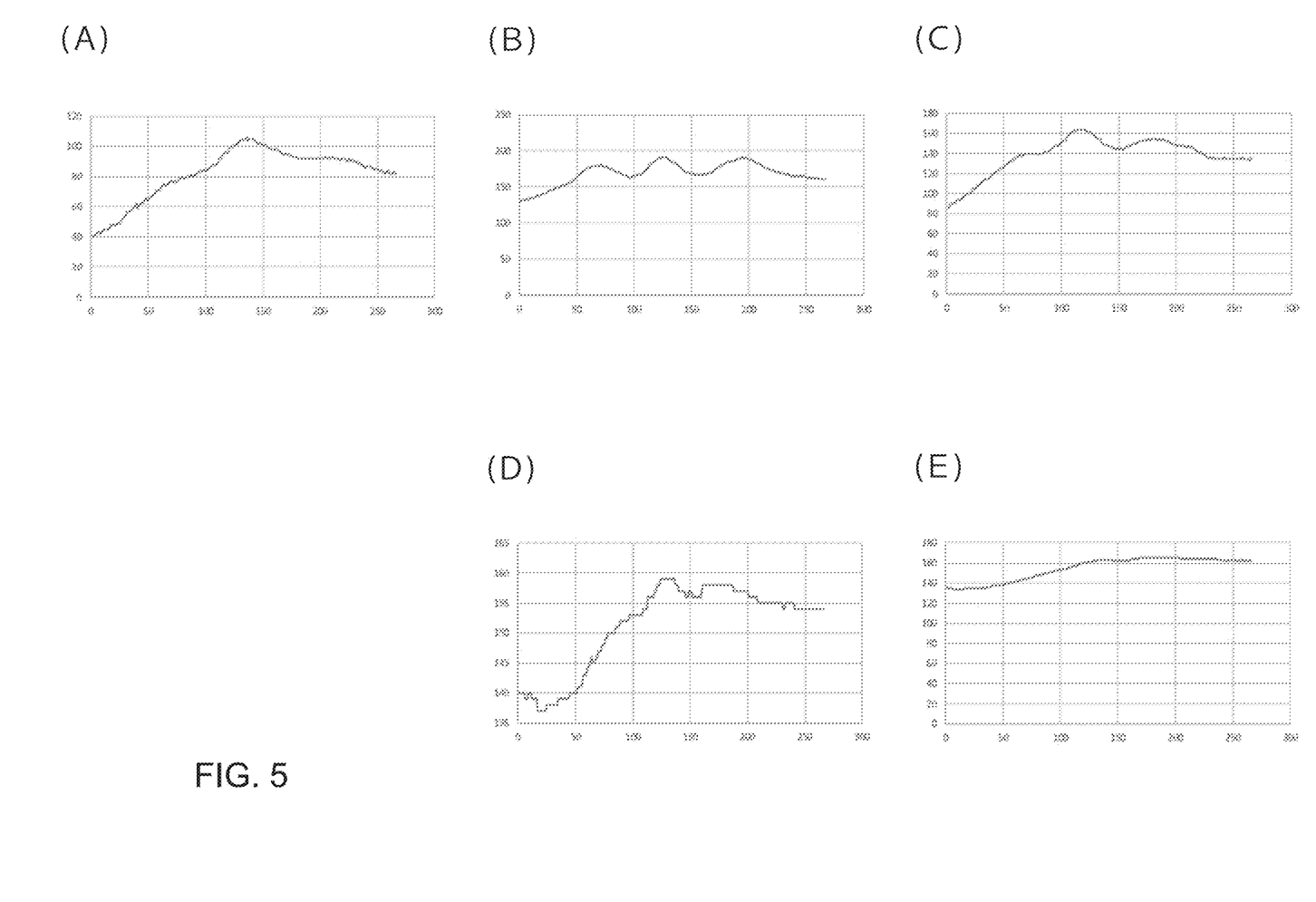
FIG. 5 is a diagram showing a density profile of an image obtained in an experiment.
Figure 6:
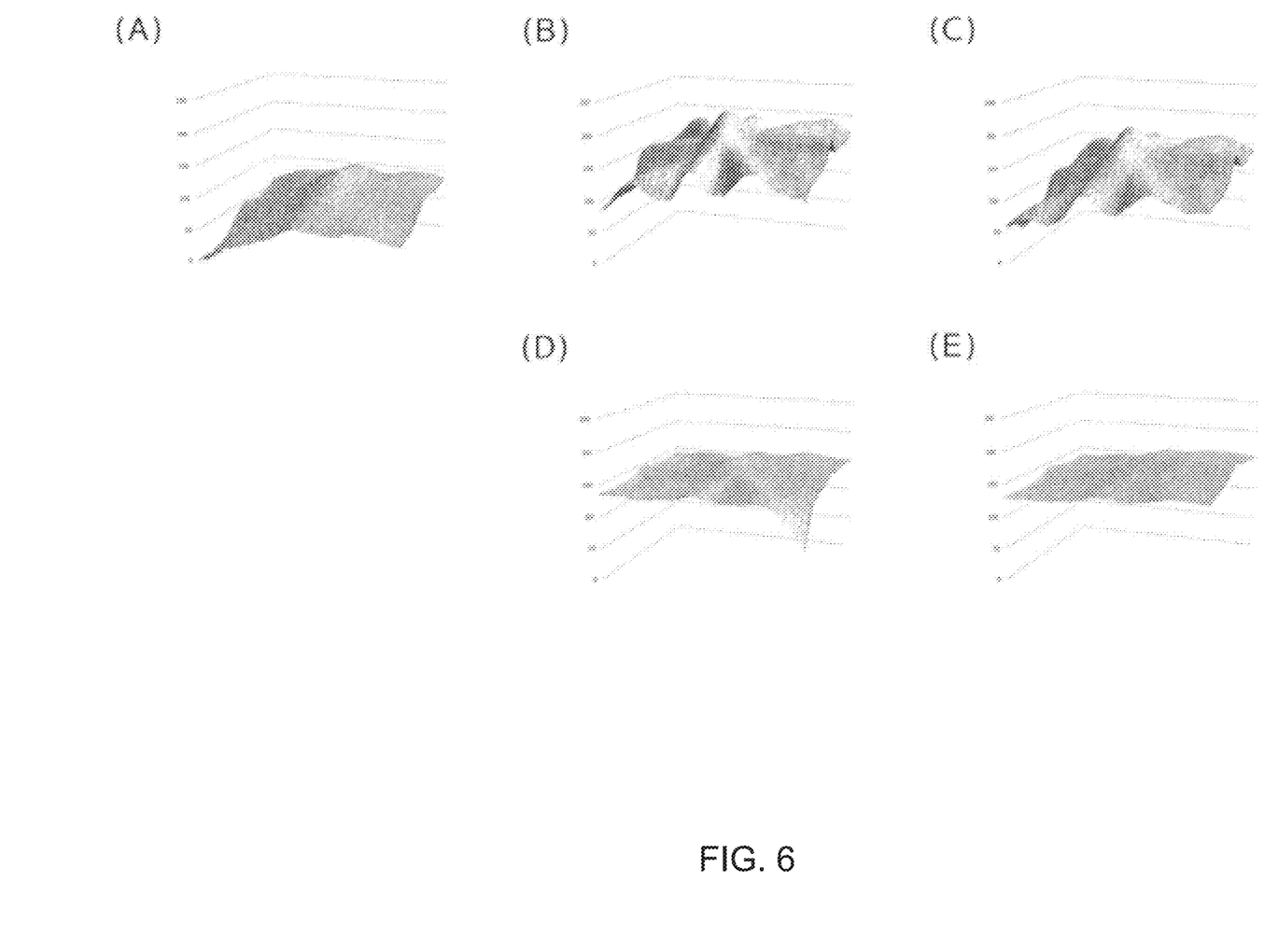
FIG. 6 is a diagram showing a density profile of an image obtained in an experiment in a three-dimensional display.

Referring to FIGS. 4 to 6, the experimental results using an inspection model (phantom) that simulates the vein of the human body will be explained.

FIG. 4 is a diagram showing an image obtained in an experiment. FIG. 4 (A) shows a vein pattern obtained in the case that the viewing angle control plate 20 is not provided, and FIGS. 4 (B) and (C) show a vein pattern obtained in the case that the viewing angle control plate 20 is disposed between the light irradiation unit 10 and the light detection unit 30, and FIGS. 4 (D) and (E) show a vein pattern obtained in the case that the viewing angle control plate 20 is disposed on the phantom side of the light irradiation unit 10.

Further, in FIGS. 4 (B) and (D), the FOP with a numerical aperture (NA) of 0.43 is used as the viewing angle control plate 20, in FIGS. 4 (C) and (E), LAF is used as the viewing angle control plate 20. In this case, the viewing angle control plate 20 has a structure in which two LAFs having a thickness of 150 μm are vertically and horizontally orthogonal to each other, and the total thickness including the adhesive layer is 360 μm. In each LAF, the light shielding portions are periodically arranged at intervals of 42 μm, FIG. 5 is a diagram showing a density profile of an image obtained in an experiment. FIGS. 5 (A)-(E) correspond to FIGS. 4 (A)-(E), respectively. FIGS. 5 (A)-(E) are profiles obtained along the I-I line, typically shown in FIG. 4 (A).

FIGS. 5 (A) to (E) show positions along the I-I line in arbitrary units on the horizontal axis, shown on the vertical axis in 256 steps, with the concentration as 0 for white and the concentration as 255 for black.

FIG. 6 is a diagram showing a density profile of an image obtained by an experiment in a three-dimensional display. FIGS. 6 (A)-(E) correspond to FIGS. 4 (A)-(E), respectively. For the two axes representing the two-dimensional position of the image, the density is shown with 256 gradations in the same manner as in FIG. 5 on the vertical axis.

The inspection model is composed of a resin which diffusely reflects infrared light at a level equivalent to that inside the human body. Inside this resin, cylindrical materials which mimic a venous blood vessel and absorb infrared light are disposed. The diameter of the cylindrical materials is 1 mm. The cross-shaped first vein pattern is arranged at a shallow position of 1 mm from the surface of the inspection model. In addition, an X-shaped second vein pattern is arranged at a depth of 2 mm from the surface of the inspection model.

As shown in FIGS. 4A and 5A, in the case that the viewing angle control plate 20 is not provided, the shallower first vein pattern can be confirmed, but the deeper second vein pattern has a blurred image.

Further, when comparing FIGS. 4 (B) and (C) and FIGS. 5 (B) and (C) with FIGS. 4 (D) and (E) and FIGS. 5 (D) and (E), the vein pattern is clear as shown in FIGS. 4 (B) and (C) and FIGS. 5 (B) and (C), that is, in the case where the viewing angle control plate 20 is disposed between the light irradiation unit 10 and the light detection unit 30.

When comparing FIGS. 4(B) and (D) and FIGS. 5(B) and (D) with FIGS. 4(C) and (E) and FIGS. 5(C) and (E), the vein pattern is clearer as shown in FIGS. 4(B) and (D) and FIGS. 5(B) and (D), that is, in the case where the FOP having an NA of 0.43 is used as the viewing angle control plate 20.

In particular, as shown in FIG. 4B, when the FOP having the NA of 0.43 is used as the viewing angle control plate 20 between the light irradiation unit 10 and the light detection unit 30, not only the shallower first vein pattern but also the deeper second vein pattern can be clearly obtained. In addition, referring to FIG. 5B, a peak corresponding to the first vein pattern and a peak corresponding to the second vein pattern on both sides thereof can be confirmed.

As described above, according to the optical sensor of the present invention, a vein pattern with high resolution can be obtained.

When irradiating light from the light irradiation unit 10 to the measurement object 100, there is also light reflected from the surface of the measurement object 100. This is because when the air layer is present between the light irradiation unit 10 and the measurement object 100, a part of the light irradiated from the light irradiation unit 10 to the measurement object 100 is reflected at the interface between the air and the measurement object 100 from the difference in the refractive index of the air and the measurement object. Reflection at this interface results in a reduction in the contrast of the image within the measurement object 100.

In order to suppress the influence of reflection at this interface, a soft resin sheet having a thickness of 10 μm to 300 μm may be provided between the light irradiation unit 10 and the measurement object 100 so as to adhere to the measurement object 100.

DESCRIPTION OF REFERENCE SIGNS

10 Light irradiation unit
12 Light source
14 Light guide plate
16 Modulation part
18 Non-modulating part
20 Viewing angle control plate
30 Light detection unit

The invention claimed is:

1. An optical sensor comprising:
   a light irradiation unit for performing uniform light irradiation with respect to a measurement object;
   a viewing angle control plate for limiting a direction of reflected light from the measurement object to a predetermined direction; and
   a light detecting unit for acquiring image information showing a distribution of the reflected light obtained through the viewing angle control plate;
   wherein the viewing angle control plate is provided between the light irradiation unit and the light detecting unit;
   wherein the viewing angle control plate is provided directly on an input side of the light detecting unit; and
   wherein the viewing angle control plate has a structure in which at least two louver array films are orthogonal to each other.

2. The optical sensor of claim 1, wherein:
   the light irradiation unit includes a light source and a light guide plate,
   light emitted by the light source spreads over an entire interior of the light guide plate,
   a modulation unit is regularly formed on one main surface of the light guide plate over the entire surface,
   conditions of total reflection of the modulation unit is different from conditions of total reflection of a non-modulation unit that is a portion of the light guide plate other than the modulation unit, and
   thereby uniformly light is irradiated from the entire surface of one of the main surfaces of the light guide plate.

3. The optical sensor of claim 2, wherein the light guide plate is made of a material having a Young's modulus of 1 MPa or more and 1000 MPa or less.

4. The optical sensor of claim 2, wherein a thickness of the light guide plate is 100 μm or more and 1 mm or less.

5. The optical sensor of claim 1, wherein the viewing angle control plate is made of a material having a Young's modulus of 1 MPa or more and 1000 MPa or less.

6. The optical sensor of claim 1, wherein a thickness of the viewing angle control plate is 1 mm or less.

7. The optical sensor of claim 1, wherein the viewing angle control plate has a numerical aperture that is 0.1 or more and 0.7 or less.

8. The optical sensor of claim 1, wherein the two louver array films have a thickness of 150 μm, respectively.

9. The optical sensor of claim 2, wherein the light sent to the light guide plate is input to an inside of the light guide plate from a side surface of the light guide plate and propagates inside of the light guide plate while totally reflecting in the two main surfaces.

10. The optical sensor of claim 1, wherein a resin sheet is provided between the light irradiation unit and the measurement object.

11. The optical sensor of claim 2, wherein:
    the modulation unit is one of a plurality of modulation units, and
    the plurality of modulation units are more densely arranged farther from the light source.

12. An optical sensor comprising:
    a light irradiation unit for performing uniform light irradiation with respect to a measurement object and including a light source and a light guide plate, wherein light is irradiated uniformly from the entire surface of one of the main surfaces of the light guide plate;
    a viewing angle control plate;
    a light detecting unit for acquiring image information showing a distribution of the reflected light obtained through the viewing angle control plate;
    wherein:
       the viewing angle control plate is positioned between the light irradiation unit and the light detecting unit;
       the viewing angle control plate is positioned directly on an input side of the light detecting unit; and
       the viewing angle control plate limits a direction of reflected light from the measurement object to a predetermined direction through a thickness of the viewing angle control plate substantially in a normal direction of an incident surface of the viewing angle control plate and the light detecting unit,
       wherein the viewing angle control plate has a structure in which at least two louver array films each having a thickness of 150 μm and are oriented orthogonal to each other.

13. The optical sensor of claim 12, wherein:
    the light irradiation unit includes a light source and a light guide plate,
    light emitted by the light source spreads over an entire interior of the light guide plate,
    a modulation unit is regularly formed on one main surface of the light guide plate over the entire surface, and
    conditions of total reflection of the modulation unit is different from conditions of total reflection of a non-modulation unit that is a portion of the light guide plate other than the modulation unit.

14. The optical sensor of claim 13, wherein the modulation unit is provided denser farther from the light source.

15. The optical sensor of claim 12, wherein a numerical aperture of the viewing angle control plate is 0.1 or more and 0.7 or less.

16. The optical sensor of claim 12, wherein the light reflected by the measurement object is transmitted only and continuously through the viewing angle control plate material and directly to the light detecting unit.

17. The optical sensor of claim 12, wherein the light guide plate is made of a material having a Young's modulus of 1 MPa or more and 1000 MPa or less.

18. The optical sensor of claim 12, wherein the viewing angle control plate is made of a material having a Young's modulus of 1 MPa or more and 1000 MPa or less.

19. The optical sensor of claim 12, wherein a resin sheet is provided between the light irradiation unit and the measurement object.

* * * * *